(12) United States Patent
Mori

(10) Patent No.: US 12,065,031 B2
(45) Date of Patent: Aug. 20, 2024

(54) FUEL CELL VEHICLE

(71) Applicant: HONDA MOTOR CO., LTD., Tokyo (JP)

(72) Inventor: Takanori Mori, Tokyo (JP)

(73) Assignee: HONDA MOTOR CO., LTD., Tokyo (JP)

( * ) Notice: Subject to any disclaimer, the term of this patent is extended or adjusted under 35 U.S.C. 154(b) by 561 days.

(21) Appl. No.: 17/375,031

(22) Filed: Jul. 14, 2021

(65) Prior Publication Data
US 2022/0016973 A1 Jan. 20, 2022

(30) Foreign Application Priority Data
Jul. 20, 2020 (JP) ................................ 2020-123750

(51) Int. Cl.
*B60K 15/03* (2006.01)
*B60L 50/70* (2019.01)
(Continued)

(52) U.S. Cl.
CPC .............. *B60K 15/03* (2013.01); *B60L 50/70* (2019.02); *B60L 58/30* (2019.02); *G01N 33/005* (2013.01); *H01M 8/22* (2013.01); *H01M 8/2475* (2013.01); *B60K 2015/03118* (2013.01); *B60L 2200/44* (2013.01); *B60Y 2200/15* (2013.01)

(58) Field of Classification Search
CPC .......... B60K 15/03; B60K 2015/03118; B60L 50/70; B60L 58/30; B60L 2200/44; G01N 33/005; H01M 8/22; H01M 8/2475
See application file for complete search history.

(56) References Cited

U.S. PATENT DOCUMENTS 8,978,617 B2 * 3/2015 Matsuda ................. F02B 77/00
                                                       180/68.5
9,260,009 B2 * 2/2016 Mizuno ................. B60K 15/07
(Continued)

FOREIGN PATENT DOCUMENTS

CN     101102914    1/2008
CN     101342863    1/2009
(Continued)

OTHER PUBLICATIONS

Japanese Office Action for Japanese Patent Application No. 2020-123750 mailed May 24, 2022.
(Continued)

*Primary Examiner* — Tony H Winner
*Assistant Examiner* — Michael R Stabley
(74) *Attorney, Agent, or Firm* — Amin, Turocy & Watson, LLP

(57) ABSTRACT

In a fuel cell vehicle, an occupant room is disposed at a front part of a vehicle body frame, and a rear side of the occupant room of the vehicle body frame is a load mount part. A hydrogen handling device is supported at least by the load mount part. The fuel cell vehicle includes a cover room that surrounds at least an upper part and a side part of the hydrogen handling device that is supported by the load mount part. A load room is disposed on the load mount part of the vehicle body frame. A discharge duct that discharges a hydrogen gas in the cover room upward from between the load room and the occupant room is connected to the cover room.

4 Claims, 2 Drawing Sheets

(51) Int. Cl.
    *B60L 58/30*      (2019.01)
    *G01N 33/00*      (2006.01)
    *H01M 8/22*       (2006.01)
    *H01M 8/2475*     (2016.01)

(56) References Cited

U.S. PATENT DOCUMENTS

| | | | |
|---|---|---|---|
| 11,359,745 | B2 * | 6/2022 | Shroff ................ G01M 3/3236 |
| 11,407,306 | B2 * | 8/2022 | Otsura ...................... B60S 5/00 |
| 2004/0026427 | A1 * | 2/2004 | Shigematsu ........... B60K 15/07 |
| | | | 220/562 |
| 2008/0156809 | A1 | 7/2008 | Mizuno et al. |
| 2013/0174804 | A1 | 7/2013 | Matsuda |

FOREIGN PATENT DOCUMENTS

| | | |
|---|---|---|
| CN | 103085652 | 5/2013 |
| CN | 103192687 | 7/2013 |
| CN | 108725184 | 11/2018 |
| CN | 111417535 | 7/2020 |
| DE | 102019004134 | 1/2020 |
| JP | 2002-089793 | 3/2002 |
| JP | 2002-096648 | 4/2002 |
| JP | 2004-136828 | 5/2004 |
| JP | 2004-161058 | 6/2004 |
| JP | 2005-033996 | 2/2005 |
| JP | 2010-070028 | 4/2010 |
| JP | 2017-128202 | 7/2017 |

OTHER PUBLICATIONS

Chinese Notice of Allowance for Chinese Patent Application No. 202110767922.5 mailed May 31, 2023.

Chinese Office Action for Chinese Patent Application No. 202110767922.5 mailed Dec. 2, 2022.

* cited by examiner

FUEL CELL VEHICLE

CROSS-REFERENCE TO RELATED APPLICATION

Priority is claimed on Japanese Patent Application No. 2020-123750, filed on Jul. 20, 2020, the contents of which are incorporated herein by reference.

BACKGROUND

Field of the Invention

The present invention relates to a fuel cell vehicle that includes a load mount part on a rear side of an occupant room.

Background

In recent years, in vehicles such as a truck in which a load mount part is disposed at the rear of an occupant room, a vehicle (hereinafter, referred to as a "fuel cell vehicle") in which a fuel cell is mounted as a drive electric power source has been developed (for example, refer to Japanese Unexamined Patent Application, First Publication No. 2005-33996).

In the fuel cell vehicle described in Japanese Unexamined Patent Application, First Publication No. 2005-33996, the occupant room is arranged at a front part of a vehicle body frame, and the rear side of the occupant room of the vehicle body frame is the load mount part. A load room is attached to the load mount part of the vehicle body frame, and a fuel cell system that includes a hydrogen tank is disposed below the load room. The hydrogen tank which is a hydrogen handling device is supported by the vehicle body frame below the load room. In this fuel cell vehicle, electric power is generated by the fuel cell system below the load room, and a motor for driving the vehicle is driven by the generated electric power.

SUMMARY

In the fuel cell vehicle described above, since the hydrogen tank (hydrogen handling device) is supported by the load mount part of the vehicle body frame, the installation height of the hydrogen tank is close to a height at which a worker who works around the vehicle. Therefore, it is desired that even if hydrogen gas leaks from the hydrogen tank, the hydrogen gas is prevented from flowing out directly to the surrounding area.

An aspect of the present invention provides a fuel cell vehicle in which, even when a hydrogen gas may be leaked from a hydrogen handling device, the leaked hydrogen gas can be prevented from flowing out directly to the surrounding area of the hydrogen handling device.

A fuel cell vehicle according to an aspect of the present invention is a fuel cell vehicle in which an occupant room is disposed at a front part of a vehicle body frame, a rear side of the occupant room of the vehicle body frame is a load mount part, and a hydrogen handling device is supported at least by the load mount part, the fuel cell vehicle including a cover room that surrounds at least an upper part and a side part of the hydrogen handling device that is supported by the load mount part, wherein a load room is disposed on the load mount part of the vehicle body frame, and a discharge duct that discharges a hydrogen gas in the cover room upward from between the load room and the occupant room is connected to the cover room.

According to the configuration described above, even when the hydrogen gas may be leaked from the hydrogen handling device, the leaked hydrogen gas can be prevented from flowing out to the surrounding area by the cover room, and it is possible to discharge the hydrogen gas in the cover room upward via the discharge duct from between the load room and the occupant room. Accordingly, when this configuration is employed, the leaked hydrogen gas from the hydrogen handling device can be prevented from flowing out to the surrounding area from the vicinity of the cover room.

The discharge duct may cause the hydrogen gas in the cover room to be discharged externally from a position higher than the load room.

In this case, even when the hydrogen gas may be leaked from the hydrogen handling device, the leaked hydrogen gas can be prevented from flowing out to the surrounding area by the cover room, and it is possible to externally discharge the hydrogen gas in the cover room via the discharge duct from the position higher than the load room. Accordingly, when this configuration is employed, the leaked hydrogen gas from the hydrogen handling device can be prevented from flowing out to a position lower than an upper part of the load room.

A plurality of cover rooms may be disposed as the cover room at a further front position than a rear wheel in a vehicle front-to-rear direction to be spaced from each other in the vehicle front-to-rear direction, a front cover room among the plurality of cover rooms and a rear cover room among the plurality of cover rooms may be connected together via a connection pipe, the front cover room may be connected to the discharge duct, and a hydrogen detection sensor that detects a hydrogen gas may be provided on an upper part of the front cover room or the discharge duct.

In this case, even when the hydrogen gas may be leaked from any of hydrogen handling devices in the front and rear cover rooms, the leakage of the hydrogen gas can be detected by a common hydrogen detection sensor.

At least two rear cover rooms may be disposed as the rear cover room to be spaced from each other in a vehicle width direction, each of the rear cover rooms may be connected to the front cover room via the connection pipe, and each connection pipe may be inclined upward toward a vehicle front side.

According to this configuration, even in a case where the hydrogen gas leaks from any of the hydrogen handling devices in the front and rear cover rooms, the leaked hydrogen gas is guided to the front cover room or to a portion where the hydrogen detection sensor that is provided on the discharge duct is present. Therefore, the leakage of the hydrogen gas from the hydrogen handling devices that are dispersedly arranged at a plurality of locations can be promptly detected by a single hydrogen detection sensor.

A fuel cell vehicle according to another aspect of the present invention is a fuel cell vehicle in which an occupant room is disposed at a front part of a vehicle body frame, a rear side of the occupant room of the vehicle body frame is a load mount part, and a hydrogen handling device is supported at least by the load mount part, the fuel cell vehicle including a cover room that surrounds at least an upper part and a side part of the hydrogen handling device that is supported by the load mount part, wherein a discharge duct that discharges a hydrogen gas in the cover room upward at a further vehicle rear side than the cover room is connected to the cover room that is arranged at a further vehicle rear side than a rear wheel, and a hydrogen detection sensor that detects a hydrogen gas is provided on the discharge duct at a further front position than a vehicle rear end of the load mount part.

According to the configuration described above, even when the hydrogen gas may be leaked from the hydrogen handling device, the leaked hydrogen gas can be prevented from flowing out to the surrounding area by the cover room, and it is possible to discharge the hydrogen gas in the cover room upward at the vehicle rearward side via the discharge duct. Accordingly, when this configuration is employed, the leaked hydrogen gas from the hydrogen handling device can be prevented from flowing out to the surrounding area from the vicinity of the cover room.

Further, the leakage of the hydrogen gas from the hydrogen handling device can be detected by the hydrogen detection sensor. In a case where another vehicle collides from the rear of the vehicle, the hydrogen detection sensor can be protected by a vehicle rear end of the load mount part. Therefore, even in a case where another vehicle collides from the rear of the vehicle, the leakage of the hydrogen gas can be detected by the hydrogen detection sensor.

In the fuel cell vehicle according to an embodiment of the present invention, since the upper part and the side part of the hydrogen handling device are covered by the cover room, even when the hydrogen gas may be leaked from the hydrogen handling device, the leaked hydrogen gas can be prevented from flowing out directly to the surrounding area of the hydrogen handling device.

DESCRIPTION OF EMBODIMENTS

Hereinafter, an embodiment of the present invention will be described with reference to the drawings.

Figure 1:
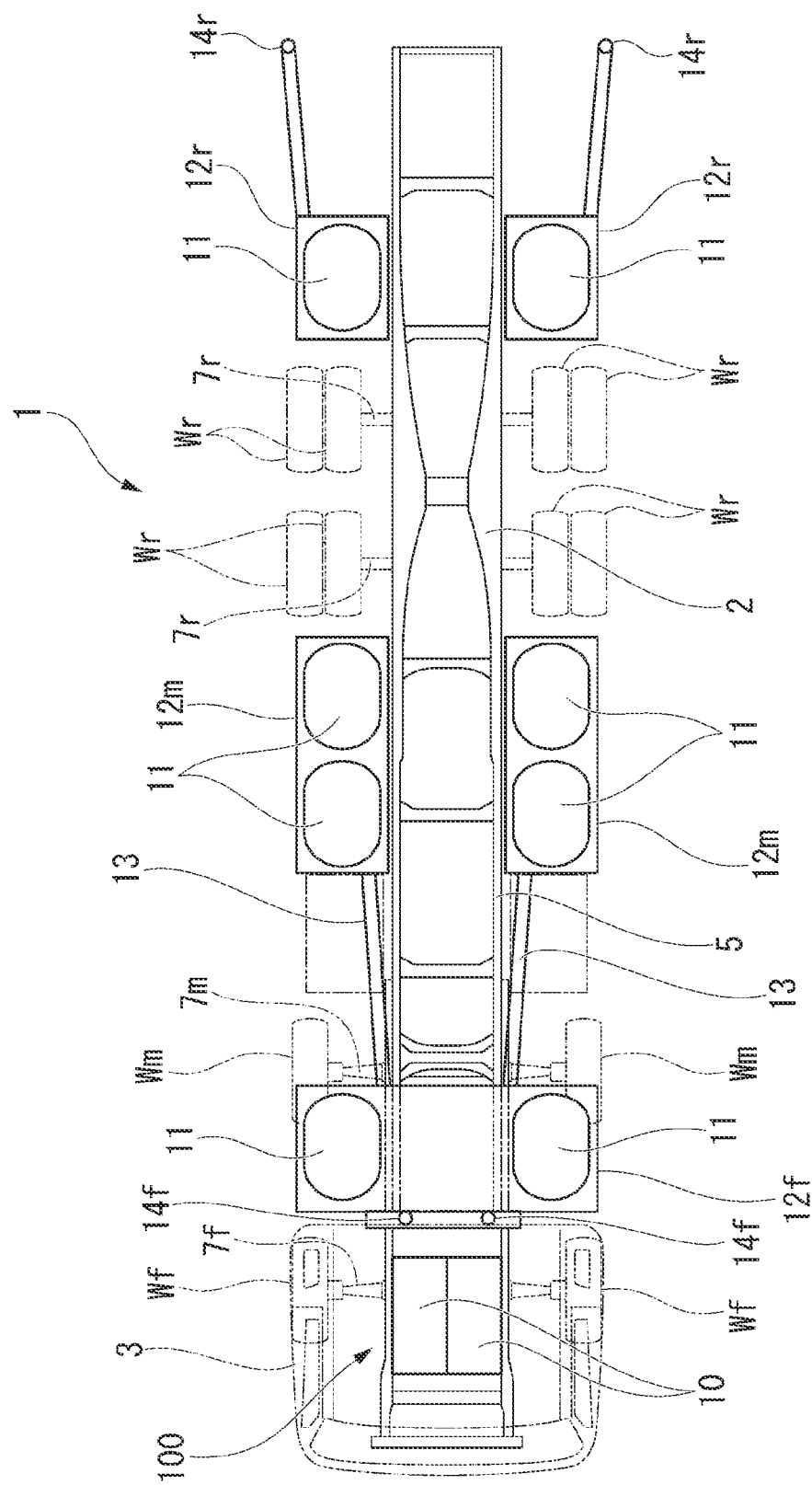
FIG. 1 is a top view of a fuel cell vehicle of an embodiment.
Figure 2:
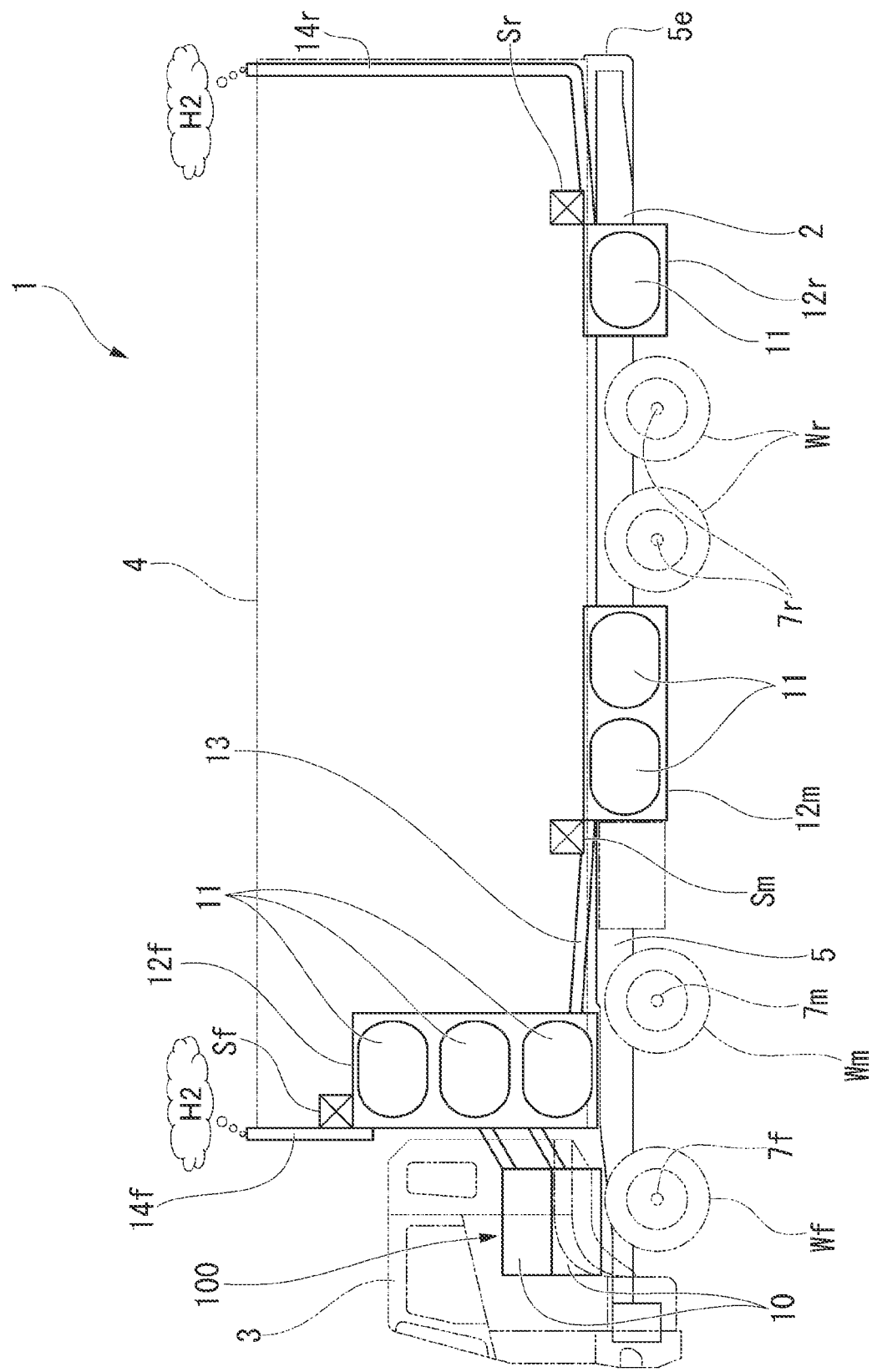
FIG. 2 is a side view of the fuel cell vehicle of the embodiment.

FIG. 1 is a plan view of a fuel cell vehicle 1 of the embodiment, and FIG. 2 is a left side view of the fuel cell vehicle 1. In these drawings, portions other than a portion relating to a vehicle body frame 2 and a fuel cell system 100 are shown by a two-dot chain line.

The fuel cell vehicle 1 of the present embodiment is a truck in which a load can be loaded. The fuel cell vehicle 1 includes the vehicle body frame 2 that extends along a vehicle body front-to-rear direction. An occupant room 3 is arranged at a front part of the vehicle body frame 2. The rear side of the occupant room 3 of the vehicle body frame 2 is a load mount part 5 on which a load room 4 is provided. A motor (not shown) for driving the vehicle and the fuel cell system 100 that supplies electric power to the motor are mounted on the fuel cell vehicle 1.

The fuel cell system 100 includes: a fuel cell stack 10 that generates electric power by electrochemical reaction of hydrogen and oxygen (air); a hydrogen tank 11 that supplies a hydrogen gas as a fuel gas to the fuel cell stack 10; and an air compressor (not shown) that supplies air (oxygen) as an oxidizer gas to the fuel cell stack 10. In the present embodiment, the hydrogen tank 11 constitutes a hydrogen handling device.

A plurality (for example, four) of fuel cell stacks 10 are arranged at a lower position of the occupant room 3. A plurality of hydrogen tanks 11 are dispersedly arranged at a front position, a middle position, and a rear position of the load mount part 5 of the vehicle body frame 2. Three hydrogen tanks 11 at the front position of the load mount part 5 are arranged in three steps in a vertical direction at an upper part on the left outside of the vehicle body frame 2 in a vehicle width direction. Similarly, three hydrogen tanks 11 at the front position of the load mount part 5 are arranged in three steps in the vertical direction also at an upper part on the right outside of the vehicle body frame 2 in the vehicle width direction. Two hydrogen tanks 11 at the middle position of the load mount part 5 are arranged in two rows in a front-to-rear direction at a lower part on the left outside of the vehicle body frame 2 in the vehicle width direction. Similarly, two hydrogen tanks 11 at the middle position of the load mount part 5 are arranged in two rows in the front-to-rear direction also at a lower part on the right outside of the vehicle body frame 2 in the vehicle width direction. One hydrogen tank 11 at the rear position of the load mount part 5 is arranged at a lower part on the left outside and at a lower part on the right outside of the vehicle body frame 2 in the vehicle width direction.

A front wheel axle 7$f$ is arranged at a lower position of the occupant room 3 of the vehicle body frame 2, and two rear wheel axles 7$r$ of front and rear sides are arranged at a rear position of the load mount part 5 of the vehicle body frame 2. One front wheel Wf is supported by each of right and left end parts of the front wheel axle 7$f$. Two rear wheels Wr are supported by right and left sides of the two rear wheel axle 7$r$, respectively. A middle wheel axle 7$m$ is arranged at a front position of the load mount part 5 of the vehicle body frame 2. One middle wheel Wm is supported by each of right and left end parts of the middle wheel axle 7$m$. A drive force of the motor for driving the vehicle is transmitted to the rear wheel axle 7$r$, for example, via a propeller shaft (not shown). A drive method of the vehicle is not limited thereto, and the front wheel axle 7$f$ may be driven by the motor for driving the vehicle.

Here, the three left hydrogen tanks 11 and the three right hydrogen tanks 11 that are arranged at the front position of the load mount part 5 are arranged at a further front position than the middle wheel axle 7$m$ and at a further rear position than the front wheel Wf.

The two left hydrogen tanks 11 and the two right hydrogen tanks 11 that are arranged at the middle position of the load mount part 5 are arranged at a further front position than the rear wheel Wr and at a further rear position than the middle wheel Wm. The one left hydrogen tank 11 and the one right hydrogen tank 11 that are arranged at the rear position of the load mount part 5 are arranged at a further rear position than the rear wheel Wr.

The three left hydrogen tanks 11 and the three right hydrogen tanks 11 that are arranged at the front position of the load mount part 5 are surrounded by a wall of a cover room 12$f$ that covers an upper part of the hydrogen tanks 11 and a side part of the surrounding area of the hydrogen tanks 11. An upper part and a side part of the surrounding area of each of the two left hydrogen tanks 11 and the two right hydrogen tanks 11 that are arranged at the middle position of the load mount part 5 are surrounded by a wall of a cover room 12$m$. An upper part and a side part of the surrounding area of each of the one left hydrogen tank 11 and the one right hydrogen tank 11 that are arranged at the rear position of the load mount part 5 are surrounded by a wall of a cover room 12$r$.

In the present embodiment, lower sides of the cover rooms 12$f$, 12$m$, and 12$r$ are also closed by a wall. However, the cover rooms 12f, 12m, and 12r may have a structure that can surround at least the upper part and the side part of the hydrogen tank 11 that is arranged at the inside.

Upper parts of the cover rooms 12m that are arranged on right and left sides at the middle position of the load mount part 5 are connected to a rear lower position of the cover room 12f at the front position by a connection pipe 13, respectively. The cover room 12m at the middle position of the load mount part 5 is arranged at a lower side of the vehicle body frame 2, and the cover room 12f at the front position of the load mount part 5 is arranged at an upper side of the vehicle body frame 2. The connection pipes 13 that extend from the upper parts of the right and left cover rooms 12m are inclined upward toward the front side of the vehicle, and front end parts of the connection pipes 13 are connected to the cover room 12f at the front position.

A pair of discharge ducts 14f are connected to a front upper end position of the cover room 12f at the front position. The pair of discharge ducts 14f extend vertically upward between the load room 4 and the occupant room 3. Upper end parts of the discharge ducts 14f extend further upward than an upper end part of the load room 4. If hydrogen gas leaks from the hydrogen tank 11 in the cover rooms 12m and 12f, the discharge duct 14f discharges the hydrogen gas to a higher position than the load room 4 from the cover room 12f at the front position.

A hydrogen detection sensor Sf that detects a hydrogen gases in the cover room 12f is provided on an upper part of the cover room 12f at the front position. If the hydrogen gas leaks from the hydrogen tank 11 at the inside of the cover room 12f at the front position or the cover room 12m at the middle position, the hydrogen detection sensor Sf detects the leaked hydrogen gas. The hydrogen detection sensor Sf is connected to a warning device (not shown) of the vehicle via a control circuit. The warning device operates when leakage of the hydrogen gas is detected by the hydrogen detection sensor Sf, and thereby, it is possible to inform the occupant of the leakage of the hydrogen gas.

In the present embodiment, the hydrogen detection sensor Sf is provided on the upper part of the cover room 12f at the front position; however, the hydrogen detection sensor Sf may be provided on the discharge duct 14f.

In the present embodiment, as shown in FIG. 2, a hydrogen detection sensor Sm is provided on the connection pipe 13 that connects the cover room 12m at the middle position to the cover room 12f at the front position. If the hydrogen gas leaks from the hydrogen tank 11 at the inside of the cover room 12m at the middle position, the hydrogen detection sensor Sm detects the leaked hydrogen gas. The hydrogen detection sensor Sm is also connected to a warning device (not shown) of the vehicle via a control circuit.

In the present embodiment, the hydrogen detection sensor Sm is provided on the connection pipe 13; however, the hydrogen detection sensor Sm may be provided on an upper part of the cover room 12m at the middle position. Further, since the hydrogen gas that leaks from the hydrogen tank 11 at the inside of the cover room 12f at the middle position is guided to the cover room 12f at the front position via the connection pipe 13, the hydrogen detection sensor Sm that is arranged at the middle position can be omitted. However, when the hydrogen detection sensor Sm is provided at the middle position as in the present embodiment, if hydrogen gas leaks from the hydrogen tank 11 in the cover room 12f, the leakage of the hydrogen gas can be promptly detected by the hydrogen detection sensor Sm.

A discharge duct 14r is connected to a rear upper end position of each of right and left cover rooms 12r at the rear position. The discharge duct 14r extends to a vehicle body rear side substantially along the vehicle body frame 2 from the rear upper end position of the cover room 12r and then extends vertically upward from the front side of a rear end part of the vehicle body frame 2. An upper end part of the discharge duct 14r extends further upward than an upper end part of the load room 4. If hydrogen gas leaks from the hydrogen tank 11 in the cover room 12r, the discharge duct 14r discharges the hydrogen gas to a higher position than the load room 4 from the cover room 12r along a rear end part of the load room 4.

A hydrogen detection sensor Sr that detects a hydrogen gas which flows through the discharge duct 14r is provided on a portion of the discharge duct 14r that extends from the cover room 12r to the vehicle body rear side. If the hydrogen gas leaks from the hydrogen tank 11 at the inside of the cover room 12r at the rear position, the hydrogen detection sensor Sr detects the leaked hydrogen gas in the discharge duct 14r. The hydrogen detection sensor Sr is connected to a warning device (not shown) of the vehicle via a control circuit. The hydrogen detection sensor Sr is arranged at a further front position than a rear end part 5e (vehicle rear end) of the load mount part 5 of the vehicle body frame 2.

As described above, in the fuel cell vehicle 1 of the present embodiment, at least the upper part and the side part of the hydrogen tank 11 which is the hydrogen handling device are surrounded by the cover rooms 12f, 12m, and 12r. Therefore, even if the hydrogen gas leaks from the hydrogen tank 11, the leaked hydrogen gas can be prevented from flowing out directly to the surrounding area of the hydrogen tank 11 by the cover rooms 12f, 12m, and 12r.

Further, in the fuel cell vehicle 1 of the present embodiment, the discharge duct 14f that discharges the hydrogen gas in the cover room 12f upward from between the load room 4 and the occupant room 3 is connected to the cover room 12f at the front position. Therefore, even if the hydrogen gas leaks from the hydrogen tank 11, the leaked hydrogen gas can be prevented from flowing out to the surrounding area by the cover room 12f, and it is possible to discharge the hydrogen gas in the cover room 12f upward via the discharge duct 14f from between the load room 4 and the occupant room 3. Accordingly, the fuel cell vehicle 1 that employs the present configuration can prevent the hydrogen gas that has leaked from the hydrogen tank 11 from flowing out to the surrounding area from the vicinity of the cover room 12f.

Further, the fuel cell vehicle 1 of the present embodiment has a structure in which the discharge ducts 14f and 14r connected to the cover rooms 12f and 12r discharge the hydrogen gas in the cover rooms 12f and 12r to a higher position than the load room 4. Therefore, even if the hydrogen gas leaks from the hydrogen tank 11 in the cover rooms 12f and 12r, the leaked hydrogen gas can be prevented from flowing out to the surrounding area by the cover room 12f, and it is possible to externally discharge the hydrogen gas in the cover rooms 12f and 12r via the discharge ducts 14f and 14r from a position higher than the load room 4. Accordingly, the fuel cell vehicle 1 that employs the present configuration can prevent the hydrogen gas that has leaked from the hydrogen tank 11 from flowing out to a position lower than an upper part of the load room 4.

Further, in the fuel cell vehicle 1 of the present embodiment, the cover room 12m at the middle position that is arranged at a further front position than the rear wheel Wr and the cover room 12f at the front position are connected together via the connection pipe 13, and the hydrogen detection sensor Sf is provided on the upper part of the cover room 12f at the front position. Therefore, even if the hydrogen gas leaks from any of the hydrogen tanks 11 in the cover rooms 12m and 12f, the leakage of the hydrogen gas can be detected by the common hydrogen detection sensor Sf.

Further, in the fuel cell vehicle 1 of the present embodiment, each of the two cover rooms 12m at the middle position is connected to the cover room 12f at the front position via the connection pipe 13, and each connection pipe 13 is arranged to be inclined upward toward the vehicle front side. Even in a case where the hydrogen gas leaks from any of the hydrogen tanks 11 in the two cover rooms 12m at the middle position and the hydrogen tank 11 in the cover room 12f at the front position, the leaked hydrogen gas is guided to the hydrogen detection sensor Sf that is arranged on the upper part of the cover room 12f at the front position. Accordingly, in the fuel cell vehicle 1 that employs the present configuration, the leakage of the hydrogen gas from the hydrogen tanks 11 that are dispersedly arranged at a plurality of locations can be promptly detected by a single hydrogen detection sensor.

Further, in the fuel cell vehicle 1 of the present embodiment, the discharge duct 14r that discharges a hydrogen gas in the cover room 12r upward at the vehicle rear side is connected to the cover room 12r at the rear position, and the hydrogen detection sensor Sr is provided on the discharge duct 14r at a further front position than the rear end portion 5e (vehicle rear end) of the load mount part 5 of the vehicle body frame 2. Therefore, when another vehicle collides from the rear of the vehicle, the hydrogen detection sensor Sr can be protected by the rear end portion 5e of the load mount part 5. Accordingly, the fuel cell vehicle 1 that employs the present configuration can detect the leakage of the hydrogen gas by the hydrogen detection sensor Sr even in a case where another vehicle collides from the rear of the vehicle.

The present invention is not limited to the embodiment described above, and various design changes can be made without departing from the scope of the invention. For example, in the embodiment described above, the upper part and the side part of the hydrogen tank which is one form of the hydrogen handling device are surrounded by the cover room; however, the hydrogen handling device is not limited to the hydrogen tank. The hydrogen handling device may be a piping, a control valve, or the like that handles hydrogen.

What is claimed is:

1. A fuel cell vehicle in which an occupant room is disposed at a front part of a vehicle body frame, a rear side of the occupant room of the vehicle body frame is a load mount part, and a hydrogen handling device is supported at least by the load mount part, the fuel cell vehicle comprising:

a cover room that surrounds at least an upper part and a side part of the hydrogen handling device that is supported by the load mount part, wherein a load room is disposed on the load mount part of the vehicle body frame, a discharge duct that discharges a hydrogen gas in the cover room upward from between the load room and the occupant room is connected to the cover room, a plurality of cover rooms are disposed as the cover room at a further front position than a rear wheel in a vehicle front-to-rear direction to be spaced from each other in the vehicle front-to-rear direction, a front cover room among the plurality of cover rooms and a rear cover room among the plurality of cover rooms are connected together via a connection pipe, the front cover room is connected to the discharge duct, and a hydrogen detection sensor that detects a hydrogen gas is provided on an upper part of the front cover room or the discharge duct.

2. The fuel cell vehicle according to claim 1, wherein the discharge duct causes the hydrogen gas in the cover room to be discharged externally from a position higher than the load room.

3. The fuel cell vehicle according to claim 1, wherein at least two rear cover rooms are disposed as the rear cover room to be spaced from each other in a vehicle width direction, each of the rear cover rooms is connected to the front cover room via the connection pipe, and each connection pipe is inclined upward toward a vehicle front side.

4. A fuel cell vehicle in which an occupant room is disposed at a front part of a vehicle body frame, a rear side of the occupant room of the vehicle body frame is a load mount part, and a hydrogen handling device is supported at least by the load mount part, the fuel cell vehicle comprising:

a plurality of cover rooms which surround at least an upper part and a side part of the hydrogen handling device that is supported by the load mount part, wherein a first discharge duct that discharges a hydrogen gas in a first cover room among the plurality of cover rooms upward at a further vehicle rear side than the first cover room is connected to the first cover room that is arranged at a further vehicle rear side than a rear wheel, a first hydrogen detection sensor that detects a hydrogen gas is provided on the first discharge duct at a further front position than a vehicle rear end of the load mount part, a second cover room and a third cover room among the plurality of cover rooms are disposed at a further front position than a rear wheel in a vehicle front-to-rear direction to be spaced from each other in the vehicle front-to-rear direction, the second cover room arranged on a front side and the third cover room arranged on a rear side are connected together via a connection pipe, the second cover room on the front side is connected to a second discharge duct that discharges a hydrogen gas in the second cover room upward from between the occupant room and a load room that is disposed on the load mount part, and a second hydrogen detection sensor that detects a hydrogen gas is provided on the second discharge duct or an upper part of the second cover room on the front side.

* * * * *